United States Patent [19]

Nash

[11] Patent Number: 5,438,976
[45] Date of Patent: Aug. 8, 1995

[54] TEETH PROTECTOR FOR LARYNGOSCOPE BLADE

[76] Inventor: Jeanne L. Nash, 10971 East Rd., Potter Valley, Calif. 95469

[21] Appl. No.: 158,957

[22] Filed: Nov. 29, 1993

[51] Int. Cl.$^6$ ............................................. A61B 1/267
[52] U.S. Cl. ................................ 600/186; 600/197; 600/199
[58] Field of Search ........................... 128/10–16, 128/200.26

[56] References Cited

U.S. PATENT DOCUMENTS

| | | | |
|---|---|---|---|
| 3,426,749 | 2/1969 | Jephcott | 128/11 |
| 3,696,811 | 10/1972 | Chen | 604/57 X |
| 3,777,754 | 12/1973 | Plachy | 604/308 |
| 3,777,759 | 12/1973 | Oehmke et al. | 604/366 |
| 3,826,248 | 7/1974 | Gobels | 128/11 |
| 4,041,937 | 8/1977 | Diaz | 128/15 |
| 4,144,658 | 3/1979 | Swan, Jr. | 36/117 |
| 4,579,108 | 4/1986 | Bauman | 128/10 |
| 4,583,527 | 4/1986 | Musicant et al. | 128/11 |
| 4,834,077 | 5/1989 | Sun | 128/11 |
| 4,878,486 | 11/1989 | Slater | 128/110 |
| 5,011,868 | 4/1991 | Keegan | 433/180 X |
| 5,038,766 | 8/1991 | Parker | 128/200.26 |
| 5,063,907 | 11/1991 | Musicant et al. | 128/10 |
| 5,065,738 | 11/1991 | Van Dam | 128/11 |
| 5,174,283 | 12/1992 | Parker | 128/200.26 |

*Primary Examiner*—Richard J. Apley
*Assistant Examiner*—Donna L. Maraglio
*Attorney, Agent, or Firm*—David Newman & Associates

[57] ABSTRACT

This invention relates to a teeth protector for a laryngoscope blade which protector comprises at least one cushioning device of deformable material deformed around at least one selected surface of the laryngoscope blade and adapted to retain a deformed shape and having a self-adhering surface character adapted to adhere to when pressed upon the selected surfaces which surfaces correspond to surfaces which would contact a patient's teeth if the at least one cushioning device were not used. The teeth protector is adaptable for use with virtually all laryngoscope blade styles. A cushioning device comprising beeswax is particularly useful in the teeth protector.

25 Claims, 4 Drawing Sheets

TEETH PROTECTOR FOR LARYNGOSCOPE BLADE

BACKGROUND OF THE INVENTION

1. Field of the Invention

This invention relates to a teeth protector for a laryngoscope blade that comprises at least one cushioning device of deformable material, deformed around at least one selected surface of the laryngoscope blade, adapted to retain the deformed shape, and having a surface character adapted to adhere to when pressed upon the selected surface about which the device is deformed and is easily releasable from the selected surface when lifted from the surface.

2. Description of the Related Art

A laryngoscope is a medical device used by anesthesiologists for administering general endotracheal anesthesia to patients by means of an endotracheal tube. An endotracheal tube allows the continuous delivery of anesthetic gases to the patient during certain surgical procedures. In order to place an endotracheal tube into the patient for the administering of anesthetic gases, one must view the larynx/vocal chords under direct visualization with a laryngoscope to ensure placement of the endotracheal tube in the trachea and not in the esophagus. Once the tube is in place, the laryngoscope is removed. The endotracheal tube remains in the patient for the duration of the surgical procedure, for as long as anesthetic gases are to be administered to the patient.

A laryngoscope is made primarily of metal, generally surgical steel, and comprises a handle and a blade portion. The handle portion is the handle for the laryngoscope and houses a power source, generally a battery, which powers a light bulb attached to the blade portion. The light bulb illuminates the inside of a patient's mouth and throat during endotracheal intubation. The blade portion generally comprises a side wall which assists in manipulating and moving the patient's tongue to the side of the patient's mouth to permit direct visualization of the larynx/vocal chords and placement of the endotracheal tube. In most all styles of blades a portion of the side wall forms a surface which makes frequent contact with a patient's upper teeth while the laryngoscope is in use. The bottom of the blade also makes contact with a patient's bottom teeth.

Many varieties of laryngoscope blades exist in the art. Some laryngoscope blades comprise a straight, generally flat blade which essentially maintains a right angle with the laryngoscope handle (e.g., the Goodwill, Foregger or Soper style blades); others comprise a slightly curved blade which curves slightly toward the handle and conforms more directly to the pathway formed in a patient's mouth and throat (e.g., the Macintosh or Bowen-Jackson style blade).

The shape of the side wall of the laryngoscope blade also varies depending on the particular style of blade. Some styles comprise a generally vertical wall and horizontal flange. In some styles the horizontal flange extends outwardly from the blade at generally a right angle to the side wall, for example, the Macintosh style blade or the Oxford Infant style blade. In other styles the horizontal flange may extend inwardly over the top of the blade at generally a right angle to the side wall; the side wall may have a rounded concave shape, for example, as found in the Seward or Miller style blades. Still other styles are flangeless blades, such as the Bizarri-Giuffrida style blade.

Virtually every laryngoscope style has a surface which contacts a patient's upper teeth and a surface which contacts a patient's bottom teeth during use. Due to the manner in which a laryngoscope blade is inserted into a patient's mouth and throat, and the manner in which a laryngoscope must remain in position during endotracheal tube placement, significant pressure is exerted on a patient's teeth, particularly the patient's upper teeth. As a result of this procedure, the upper teeth of a patient are very often chipped, and even broken.

Several devices in the art have attempted to minimize the damage to a patient's teeth as a result of the use of a laryngoscope, for example, varying the shape and style of the laryngoscope blade as described above. The slightly curved blade which more closely conforms to the pathway of a patient's mouth and throat is said to exert less pressure inside the patient's mouth during use because of the curvature of the blade. Additionally, several devices known in the art serve to cover the blade in some fashion to lessen the severity of the contact of the blade in the patient's mouth and throat. Some versions of such devices cover the entire blade, for example, the devices described in U.S. Pat. No. 3,426,749 of Jephcott, U.S. Pat. No. 4,579,108 of Bauman, U.S. Pat. No. 4,834,077 of Sun, and U.S. Pat. No. 4,878,486 of Slater.

Some devices cover only portions of the laryngoscope blade. One such device is described in U.S. Pat. No. 4,583,527 of Musicant et al. which describes a disposable cushioning device comprising an elongated sheath which is slidably and removably coupled to the blade to which a separate layer of plastic material is adhered. Another device is described in U.S. Pat. No. 5,065,738 of Van Dam which describes a blade sheath of padding having an adhesive surface and a portion which receives the tip of the laryngoscope blade and extends along the leading edge and teeth/contact areas. One further version, described in U.S. Pat. No. 3,826,248 of Gobels, utilizes an elastic material which is inlaid into the top portion of the blade.

The devices, such as those described above, do not satisfactorily address the need to protect a patient's teeth, as well as the needs of convenience and feasibility of use. First, devices which are cumbersome to apply to the laryngoscope blade are impractical. Often anesthesiologists are required to insert a laryngoscope quickly in an emergency medical situation. Blade covers which require substantial manipulation for application to the blade cause an anesthesiologist to spend too much time on preparing the laryngoscope, for example, if one must slide the device onto the blade or remove adhesive strips.

Second, the blade cover must be easy to remove and not leave permanent residue on the blade after removal of the blade cover. The blade cover must also not leave harmful or substantial residue on a patient's teeth or in a patient's mouth. While a blade cover is generally used only once, a laryngoscope blade is reusable and is sterilized between uses. Adhesives used in applying a blade cover to a blade often make it difficult to remove the blade cover, and may cause remnants of the cover to remain on the blade after the cover is removed. Third, the use of adhesives, e.g., certain glues and solvents, in a sterile medical setting is undesirable. Some such substances are flammable or have a strong odor. Fourth, many blade covers, especially those cover styles which surround the entire blade, occupy too much space in a patient's mouth, making manipulation of the laryngoscope blade and introduction of the endotracheal tube difficult. Additionally, the laryngoscope blade is much easier to insert into a patient if a significant portion of the tongue-contacting surface of the blade is smooth and unencumbered. Because insertion and manipulation of the laryngoscope blade is particularly difficult on patients who have malformed or misaligned teeth, smooth and unencumbered surfaces can assist in introducing the blade in these instances. Finally, many of the blade covers described in the art are suitable for only one type of laryngoscope blade and are not compatible or interchangeable with other blade styles.

It is therefore an object of this invention to provide a teeth protector for a laryngoscope blade which is easy and convenient to apply and remove.

It is a further object of this invention to provide a teeth protector for a laryngoscope blade which is safe to use and is also disposable.

It is a further object of this invention to provide a teeth protector for a laryngoscope blade which is compact as well as effective as a teeth protector so that as little space as possible in a patient's mouth is occupied by the teeth protector.

It is a further object of this invention to provide a teeth protector for a laryngoscope blade which is suitable for use on virtually every style of laryngoscope blade, thus eliminating the need for a different style teeth protector for each style laryngoscope blade.

Other objects and advantages will be more fully apparent from the following disclosure and appended claims.

SUMMARY OF THE INVENTION

The present invention provides a teeth protector for a laryngoscope blade. During endotracheal intubation by use of a laryngoscope blade, certain surfaces of the laryngoscope blade contact a patient's upper and bottom teeth. While both the upper and bottom teeth of a patient are contacted by the blade during use, it is often a patient's upper teeth which receive the most contact. A patient who has misaligned or malformed teeth, upper or bottom, may experience more severe contact with the blade. The use of the laryngoscope blade often causes a patient's teeth, particularly the upper teeth, to be chipped or broken. The present invention comprises a teeth protector for a laryngoscope blade which assists in protecting a patient's teeth during use of the laryngoscope. The teeth protector of the invention comprises at least one cushioning device of deformable material deformed around at least one selected surface of the laryngoscope blade. The at least one cushioning device of the teeth protector is applicable to virtually all selected teeth-contacting surfaces of the various blade styles which surfaces correspond to surfaces which would contact a patient's teeth if the cushioning device were not used on the laryngoscope blade. The remaining portions of the blade are unencumbered by the teeth protector. The cushioning device of the teeth protector is adapted to retain its deformed shape and has a surface character which is self-adhering, i.e., is adapted to adhere to when pressed upon the blade surface. The cushioning device does not, therefore, require the use of an adhesive or additional attachment means. The cushioning device is easily removed from the blade by exerting slight pressure to lift the device from the blade. Upon removal from the blade, the cushioning device does not leave residue on the blade or in a patient's mouth. The cushioning device is comprised of at least one layer. In alternative embodiments two or more layers are utilized. It should be appreciated that the invention recognizes that cushioning devices for different selected surfaces may comprise a different number of layers. The number of layers used varies with the desired thickness of the cushioning device on a particular selected surface.

The invention also recognizes that the cushioning device of the teeth protector when comprised of beeswax is a particularly beneficial. Beeswax is a deformable material, is capable of retaining a deformed shape, and has a self-adhering surface character such that the device adheres to when pressed upon a selected surface of a laryngoscope blade, and such that it is easily removed from the surface when lifted from the surface. It is appreciated that a natural or synthetic material having these characteristics (i.e., is deformable, is capable of retaining a deformed shape, and has a surface character adapted to adhere to when pressed upon a selected surface of a laryngoscope blade) is equally suitable in the teeth protector. Beeswax is a natural substance, is biodegradable and recyclable. The beeswax may be melted and reused in the teeth protector. Additionally, the beeswax optionally contains a softening agent, such as vegetable or mineral oil, to enhance the pliability of the beeswax without hindering the desired characteristics of the teeth protector. These features make beeswax particularly suitable for use in the teeth protector. Additionally, the bee glue found in beeswax is bacteriostatic, making the substance particularly suitable for use in a sterile environment.

Other aspects and features of the invention will be more fully apparent from the following disclosure and appended claims.

DETAILED DESCRIPTION OF THE INVENTION AND PREFERRED EMBODIMENTS THEREOF

Figure 1:
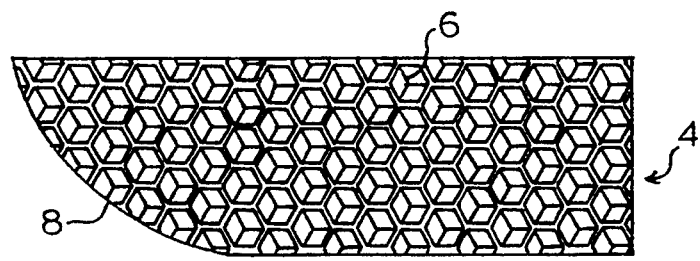
FIG. 1 is a detailed top view of an undeformed single layer of a cushioning device of a teeth protector according to the invention.
Figure 7:
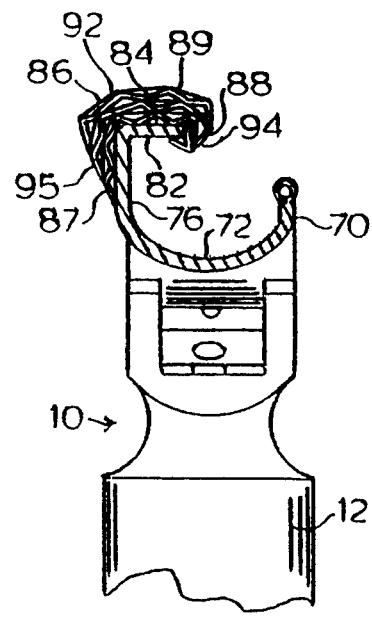
FIG. 7 is a cross-section view of the laryngoscope blade of FIG. 6 taken along line 7—7 in FIG. 6.

As will be apparent from the description and figures, the present invention is adaptable for virtually every style of laryngoscope blade. For illustrative purposes two embodiments of the invention will be shown on two different styles of laryngoscope blades, it being understood that other embodiments of the invention are possible, and that the embodiments shown in connection with a certain style blade are suitable for use on different styles of blades. FIG. 1 illustrates a detailed top view of one layer of a cushioning device of the teeth protector. FIGS. 2-5 illustrate a first embodiment of the invention as utilized with a Macintosh curved style blade; FIGS. 6-7 illustrate a second embodiment of the invention as utilized with a Miller straight style blade. It will be appreciated that the invention is easily adaptable to other style blades and that other embodiments of the invention, while not specifically illustrated herein, are encompassed by this disclosure.

The teeth protector of the invention comprises at least one cushioning device applied to at least one selected surface of a laryngoscope blade. The at least one cushioning device of deformable material is deformed around a selected surface of the blade and retains the deformed shape. The at least one cushioning device has a self-adhering surface character such that it adheres to when pressed upon the selected surface and is easily removed from the surface when lifted from the surface. The at least one cushioning device comprises at least one layer. A single layer of a cushioning device which is not yet deformed is shown in FIG. 1. Layer 4 of FIG. 1 is an elongated strip with tapered edge 8 and is shaped to correspond generally to the shape and size of a selected surface of a laryngoscope blade. However, one size and shape of layer 4 is adaptable to selected surfaces of virtually all blade styles. A smaller sized layer 4 is adaptable to an infant style laryngoscope blade. The precise dimensions of layer 4 are not critical.

Patterns 6 are optionally formed in layer 4 to provide increased cushioning to the teeth protector. These patterns may be derived from the natural honeycomb pattern formed in beeswax. Naturally occurring beeswax comprises a three-dimensional hexagonal shape, or honeycomb shape, as pattern 6. Wax manufacturers produce beeswax with different patterns, for example, triangular patterns, and are equally suitable for use in the teeth protector.

The invention recognizes the particular advantage of layer 4 being comprised of beeswax. As previously described, beeswax is a deformable material, is capable of retaining a deformed shape and is self-adhering. The invention recognizes the suitability of other natural or synthetic substances which have those characteristics (i.e., deformable, capable of retaining a deformed shape, and having a surface character which is self-adhering). The beeswax compositions comprising layer a vary in components. Beeswax compositions which contain too much paraffin are brittle in the cooler temperatures usually found in operating rooms. Softening agents are optionally added to the beeswax composition in an amount sufficient to increase the pliability of the teeth protector without hindering the desired qualities of the teeth protector (i.e., deformable, capable of retaining a deformed shape and having a self-adhering surface character). Softening agents such as vegetable oil or mineral oil are suitable for use in the layers 4 of the cushioning devices of the teeth protector. In a preferred embodiment, layers 4 of the cushioning device of the teeth protector are comprised entirely of beeswax.

Figure 2:
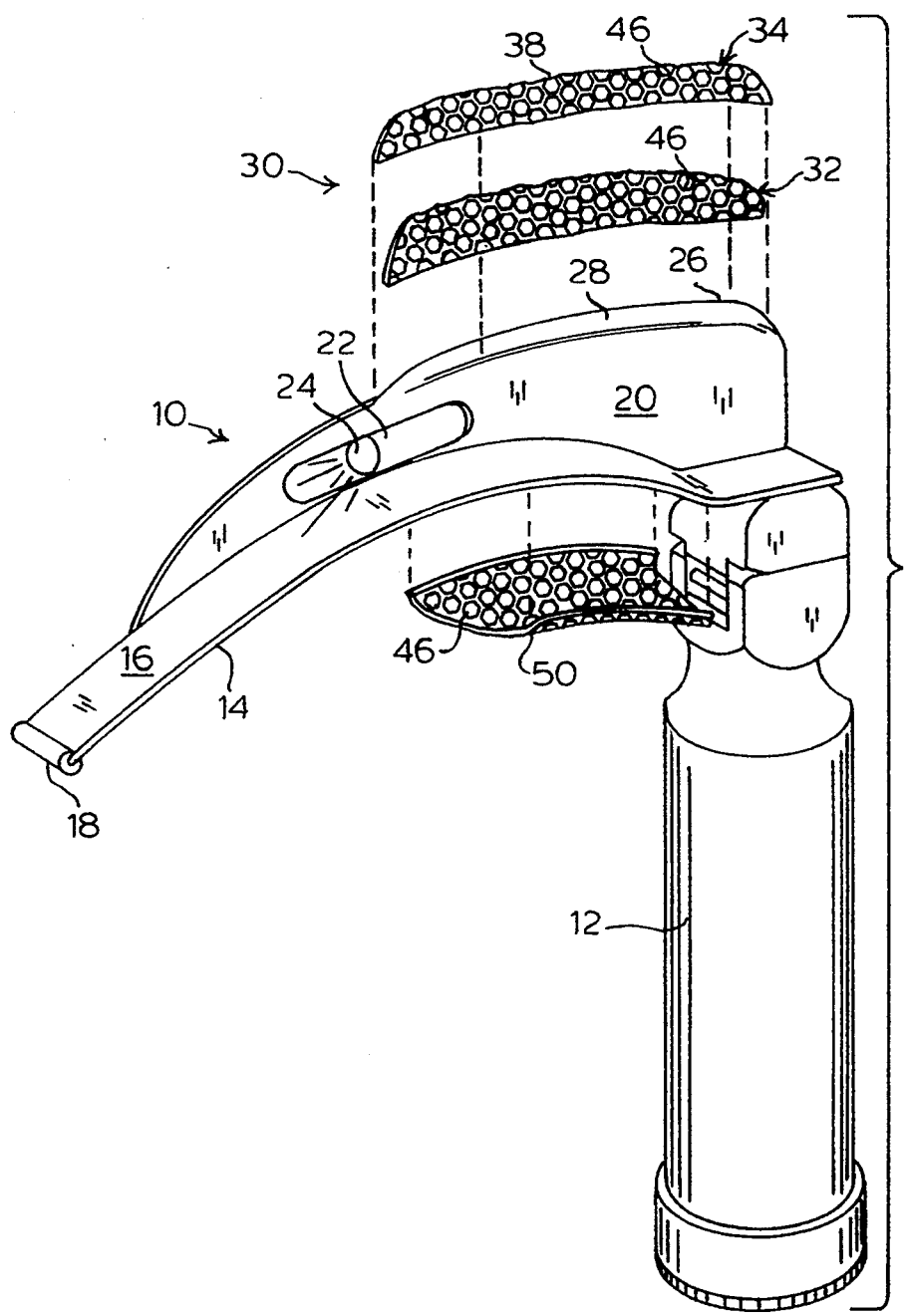
FIG. 2 is a partially-exploded top perspective view of a laryngoscope indicating the orientation of several cushioning devices according to a first embodiment of the invention prior to its being positioned upon selected teeth contacting surfaces of the laryngoscope blade. The blade shown is a Macintosh style blade.

Referring to FIGS. 2-5, laryngoscope 10 generally comprises laryngoscope handle 12, laryngoscope blade 14, and light bulb 24 to perform endotracheal intubation for anesthetization of patients. As shown in FIG. 2, the orientation of laryngoscope 10 is such that laryngoscope blade 14 extends laterally from the longitudinal axis of laryngoscope handle 12, and is positioned upwardly of handle 12. This orientation shall be referred to throughout the following description.

Figure 3:
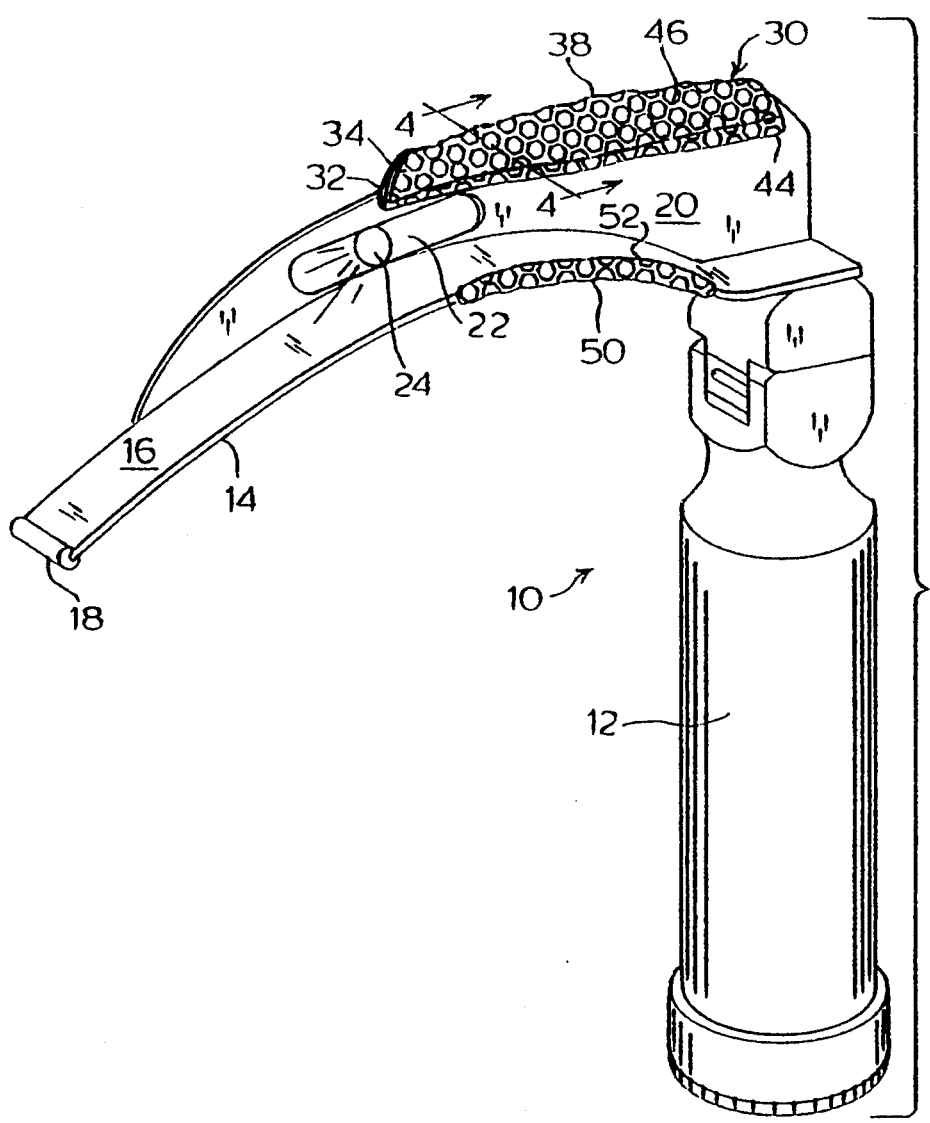
FIG. 3 is a perspective view of the laryngoscope blade of FIG. 2 showing the embodiment of the invention in position on the selected teeth contacting surfaces of the laryngoscope blade.
Figure 4:
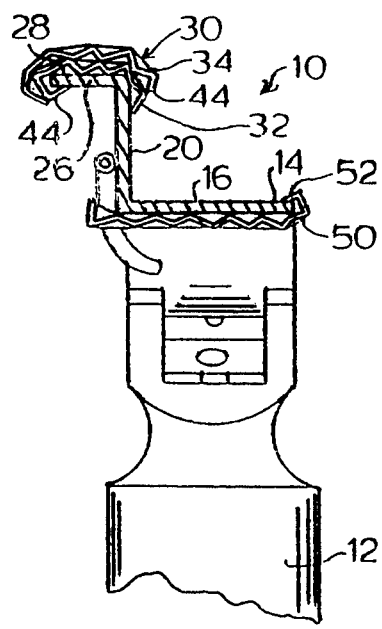
FIG. 4 is a cross-section view of the laryngoscope blade in FIG. 3 taken along line 4—4 in FIG. 3.

Housed in laryngoscope handle 12 is a battery, not shown, which is electrically connected to and powers light bulb 24 of laryngoscope blade 14 when laryngoscope 10 is in use. When not in use laryngoscope blade 14 pivots and rests in parallel fashion against handle 12 (not shown). When in use blade 14 is pushed into position, perpendicular to handle 12, as shown in FIGS. 2 and 3. In the perpendicular position blade 14 is in electrical contact with the power source in handle 12 such that bulb 24 is lit. Laryngoscope blade 14 generally comprises blade floor 16, blade tip 18, side wall 20, bulb receptacle 22 and flange 26. Blade floor 16 extends from that portion of laryngoscope blade 14 which is mounted to handle 12 to blade tip 18. Side wall 20 extends upwardly at generally a right angle from blade floor 16. Bulb receptacle 22 into which light bulb 24 is inserted is formed in side wall 20, shown inserted in FIGS. 2 and 3. Flange 26 extends away from side wall 20 at generally a right angle to side wall 20. Flange 26 forms a generally flat surface 28.

In the first embodiment of the invention shown in FIGS. 2-5, the teeth protector is comprised of cushioning device 30 and cushioning device 50. The teeth contacting surfaces of laryngoscope blade 14 correspond to surface 28 which contacts a patient's upper teeth, and the bottom surface of blade floor 16 which contacts a patient's bottom teeth. The teeth protector is applied to selected surfaces of blade 14, i.e., surface 28 or the bottom surface of blade floor 16. In this embodiment, the teeth protector comprises cushioning devices on both selected surfaces, it being understood that the invention recognizes that a cushioning device may be applied to one or the other surfaces alone.

In FIG. 2, cushioning devices 30 and 50 are shown in position prior to application to blade 14. Cushioning device 30 is comprised of a first layer 32 and a second layer 34. Cushioning device 50 comprises a single layer. As seen in FIGS. 2 and 3, cushioning device 30 is applied to surface 28, and cushioning device 50 is applied to the bottom surface of blade floor 16.

The layer 4 as discussed above forms the layers of cushioning devices 30 and 50. The invention recognizes the advantages of the cushioning devices 30 and 50 being of a deformable material and having a self-adhering surface character, as previously discussed. Because cushioning devices 30 and 50 are made from the layers which are deformable and self-adhering, they are easily and conveniently applied to flange 26. They are also capable of being quickly applied and need not be precisely or accurately placed or aligned on blade 14 in order to be effective. In a preferred embodiment cushioning devices 30 and 50 contain patterns 46, at least in the layer which contacts a patient's teeth (e.g., layer 34), to enhance the cushioning effect of the cushioning devices 30 and 50 against a patient's upper and bottom teeth, respectively.

Layers 32 and 34 of teeth protector 30 comprise an elongated strip of material as shown in FIG. 1. As previously discussed in relation to layer 4 of FIG. 1, the size and shape of layers 32 and 34 need not be precisely sized to be effective in the teeth protector. Layers which comprise the cushioning devices 30 and 50 of the teeth protector must be sized so that the cushioning devices are deformable around a substantial portion of the selected surface in a manner sufficient to provide a cushion to the teeth. Cushioning devices 30 and 50 are comprised of deformable material and deformed around selected surfaces 28 and bottom of blade floor 14 respectively. The devices 30 and 50 retain the deformed shape and have a self-adhering surface character adapted to adhere to when pressed upon the surface about which the device is deformed. Additionally, a layer of one size and shape is adaptable for use on virtually all styles of laryngoscope blades. While the approximate dimensions of a typical layer are given, it is appreciated that smaller dimensions are appropriate for an infant style laryngoscope blade, and that the dimensions are not critical. As shown in FIGS. 2–5, layers 32 and 34 have the approximate dimensions of 1¼ cm in width (approximately 0.5 inches), tapering slightly to correspond to the shape of the flange 26; 7–8 cm in length (approximately 3 inches) and ½ cm in thickness (approximately ¼ inch).

Cushioning devices 30 and 50 are disposable which feature lessens the danger of cross-contamination between patients. Cushioning devices 30 and 50 are easily trimmed with scissors. Depending on the desired thickness of cushioning devices 30 and 50, several layers may be applied to the selected surfaces of blade 14 to form the teeth protector of the invention.

When the cushioning device of the invention is comprised of more than one layer the layers may be applied sequentially upon the selected surface. Layers 32 and 34 of cushioning device 30 are capable of being sequentially applied to blade 14 prior to use, or may be secured together and applied to blade 14 as a single unit. It is recognized that more than two layers are capable of being handled in a similar manner. Layers 32 and 34 are deformed around flange 26 and once applied retain the deformed shape. The layers 32 and 34 self-adhere to flange 26 upon pressure being applied to the layers 32 and 34 against and around flange 26. To further secure cushioning device 30 to blade 14, edges 44 are molded around the perimeter of flange 26.

Cushioning device 50 of the teeth protector is deformed around the bottom surface of blade floor 14 and retains its deformed shape. Upon pressing cushioning device 50 against the bottom surface of blade floor 14, cushioning device 50 adheres to the bottom of blade floor 16. To further secure cushioning device 50 to blade 14, edges 52 are molded around the adjacent edges of blade floor 16. In this manner a patient's bottom teeth which are contacted by the blade are protected by the teeth protector of the invention. The portion of blade floor 16 covered by cushioning device 50 extends approximately from the middle portion of the blade to the back portion of blade floor 16 adjacent handle 12. It is important that cushioning device 50 not encroach upon the front tip area of the blade 14 so that insertion and manipulation of blade 14 in a patient's mouth is unencumbered.

Figure 5:
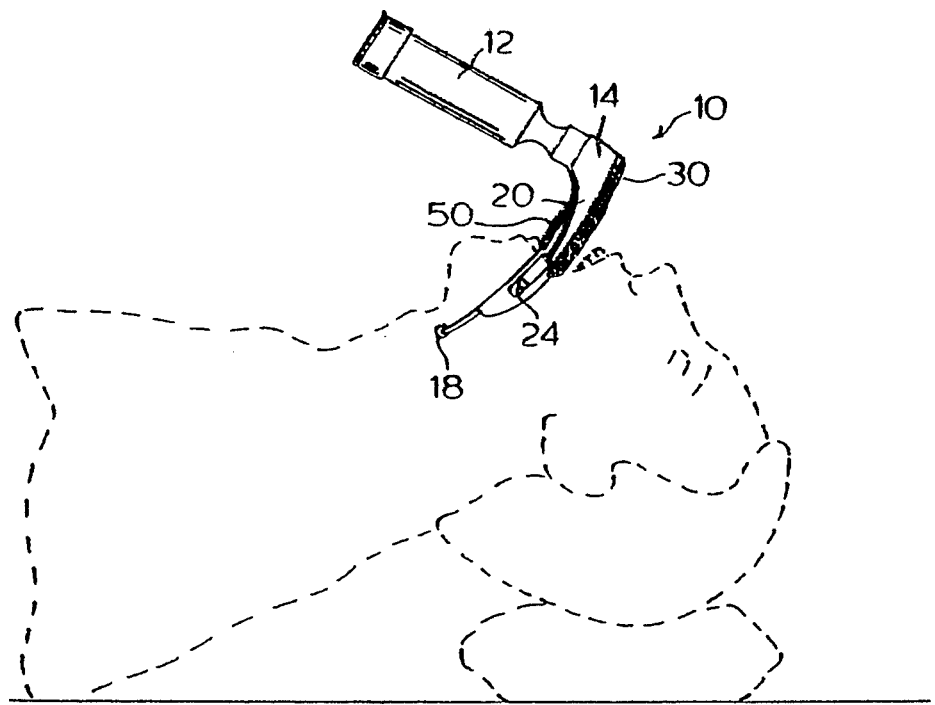
FIG. 5 is a side view showing the position of the laryngoscope and the embodiment of the invention shown in FIG. 3 during endotracheal intubation of a patient who is shown in phantom.
Figure 6:
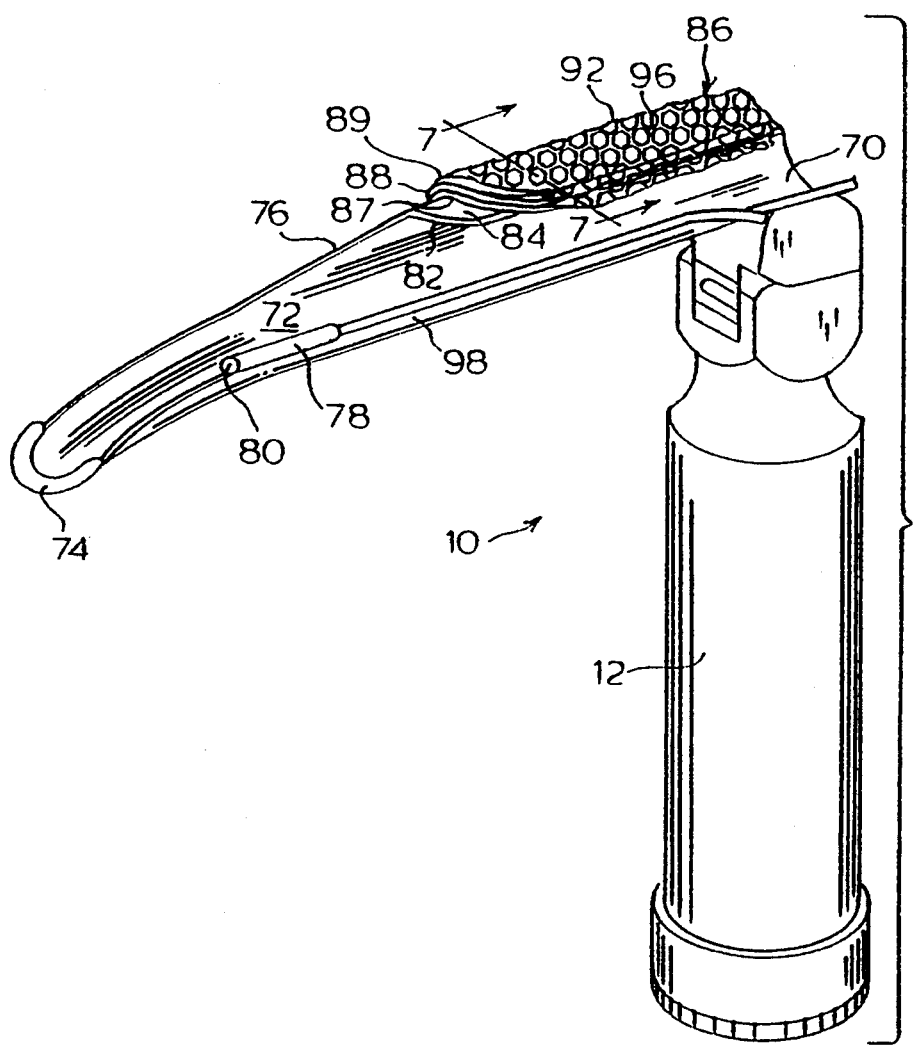
FIG. 6 is a top perspective view of a second embodiment of the invention utilized on different style laryngoscope blade than the blade shown in FIGS. 2 through 5. The blade illustrated is a Miller type blade.

When laryngoscope 10 is in use laryngoscope blade 14 is inserted into the mouth and throat of a patient, shown inserted in FIG. 5. Upper surface 38 of layer 34 of cushioning device 30 is adjacent to, and when in use, contacts a patient's upper teeth. Similarly, cushioning device 50 is applied to the bottom of blade floor 16 to cushion the contact of blade 14 and a patient's lower teeth. Cushioning devices 30 and 50 serve to protect a patient's teeth from chipping and breaking by softening and cushioning the contact between the metal blade 14 and the patient's teeth. Because cushioning devices 30 and 50 are applied only to essentially upper surface 28 of flange 26, and the bottom surface of blade floor 16, respectively, the remaining surfaces of laryngoscope blade 14 are unencumbered, smooth metal surfaces. This condition makes insertion and manipulation of laryngoscope blade 14 in a patient's mouth and throat much easier. If the patient's tongue is dry, or if the patient's teeth are malformed or misaligned, a teeth protector which covers a significant portion of the tongue-contact surface of the blade, or surrounds too much surface area of the blade, causes the blade to be difficult to insert and manipulate in the patient's mouth and throat. When blade 14 is removed from a patient's mouth, cushioning devices 30 and 50 release easily from patient's teeth and do not leave harmful or substantial residue in or on the patient's mouth or teeth.

After use, cushioning device 30 is lifted from blade 14 by unrolling edges 44 (FIG. 3) from the perimeter of flange 26 and lifting cushioning device 30 from flange 26. After removal of cushioning device 30, laryngoscope blade 14 is sterilized for reuse. Cushioning device 30 is discarded or recycled after appropriate sterilization. A particular advantage of the use of beeswax for cushioning device 30 is its capability of being remelted for reuse. Similarly cushioning device 50 is removed and discarded or recycled.

A second embodiment of the invention is shown on a straight blade style laryngoscope blade, e.g. a Miller blade in FIGS. 6 and 7. The same laryngoscope handle is utilized in FIGS. 6 and 7 as is shown in FIGS. 2–5 and is designated by the same reference number. The differences between laryngoscope blade 70 of FIGS. 6–7 and laryngoscope blade 14 of FIGS. 2–5, and the utilization of the invention on these style blades is discussed below. It is appreciated that the discussion above regarding the advantages of the teeth protector of the first embodiment are similarly applicable to the second embodiment of the invention although such discussion has not been repeated below.

Laryngoscope blade 70, shown generally in FIG. 6, comprises blade floor 72 having blade tip 74. Side wall 76 extends upwardly and curves away from blade floor 72. Bulb receptacle 78, into which light bulb 80 is attached, is formed in wall 98 on the opposite side of blade 70 from side wall 76. Flange 82 extends inwardly over blade floor 72 from side wall 76, contrary to the first style blade of FIGS. 2–5 where flange 26 extends outwardly from blade floor 14 in the laryngoscope blade. Flange 82 forms a generally flat surface 84, shown in cross-section in FIG. 7.

In this second embodiment, the teeth protector of the invention is comprised of cushioning device 86 which comprises layers 87, 88 and 89. Layer 87 is deformable around and self-adhering to surface 84 of flange 82. Layer 88 is deformable around and self-adhering to layer 87, and similarly layer 89 is deformable around and self-adhering to layer 88. When layers 87, 88 and 89 are deformed around flange 82, edges 94 are formed generally around the perimeter of flange 82 to assist in securing cushioning device 86 to flange 82 of laryngoscope blade 70. The outer edges 95 extend down along side wall 76. Optionally edges 95 extend to and wrap around the tongue side of blade 70 to the bottom surface of blade floor 72 to give further lower teeth protection (not shown). Alternatively, a second cushioning device, (not shown) such as cushioning device 50 in FIGS. 2–5, is optionally used on the bottom surface of blade floor 72 to provide lower teeth protection.

In this second embodiment, cushioning device 86 comprises three layers, although as previously stated, the first embodiment of the teeth protector of the invention shown in FIGS. 2–5 comprising two layers is similarly utilizable on the style blade shown in FIGS. 6–7. Similarly the second embodiment of FIGS. 6–7 is usable on the blade style of FIGS. 2–5. In the second embodiment shown in FIGS. 6–7, it is preferred that protector 86 be comprised of layers with patterns 96 to enhance the cushioning effect of cushioning device 86, particularly the uppermost layer 89, which forms teeth contacting surface 92 of cushioning device 86. The application and removal of cushioning device 86 is similar to the application and removal of cushioning devices 30 and 50 previously described. Cushioning device 86 is applied to flange 82 by deforming layer 87 around flange 82 and pressing layer 87 against flange 82. To further secure cushioning device 86 to flange 82, layers 87, 88 and 89 are formed around the perimeter of flange 82 to form edges 94, and edges 95 on side wall 76. As previously described, this arrangement enables as little space as possible to be occupied by cushioning device 86 in a patient's mouth. Cushioning device 86 is removed by unrolling edges 94 from flange 82 and lifting layer 87, 88 and 89 from flange 82.

A further embodiment of the teeth protector (not shown) relates to a teeth protector for a flangeless blade, such as the Bizarri-Giuffrida style blade. A flangeless blade is constructed similarly to the blades of FIGS. 2–7 except that flange 26 and flange 82 are not present, and the blade ends at a side wall edge. The teeth protector of this embodiment comprises at least one cushioning device applied to selected surfaces of the flangeless blade which correspond to the teeth contacting surfaces of the blade. A first cushioning device is applied to and deformed around the top edge of the side wall, and a second cushioning device is applied to and deformed around the under surface of the blade floor. Alternatively, a single cushioning device is simultaneously applied to and deformed around the top edge of the side wall and the bottom surface of the blade floor. In all embodiments the tip and front portions of the blade remain unencumbered by the teeth protector.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. An improved laryngoscope blade for use on a laryngoscope for performing endotracheal intubation of a patient comprising:
   a. a laryngoscope blade having a front tip area, a middle portion, a back end and at least one selected surface; and
   b. a teeth protector comprising at least one cushioning device made of a deformable material such that the at least one cushioning device is capable of being deformed about the at least one selected surface of the laryngoscope blade and retains a deformed shape, the deformable material being adherent along the entire surface thereof such that the at least one cushioning device adheres to the at least one selected surface of the blade about which the cushioning device is deformed when pressed thereupon, the at least one selected surface beginning at the back end of the blade and ending at the middle portion of the blade, the deformable material further being easily removable from the at least one selected surface after use of the blade with the patient.

2. The teeth protector of claim 1 wherein the teeth protector comprises a first cushioning device applied to a first selected surface of the laryngoscope blade and a second cushioning device applied to a second selected surface of the laryngoscope blade.

3. The teeth protector of claim 1 wherein the at least one cushioning device comprises beeswax.

4. The teeth protector of claim 1 further comprising a softening agent in the beeswax.

5. The teeth protector of claim 1 wherein the softening agent is a substance selected from the group consisting of vegetable oil and mineral oil.

6. The teeth protector of claim 1 further comprising a pattern formed in the at least one cushioning device.

7. The teeth protector of claim 1 wherein the at least one cushioning device comprises a single layer.

8. The teeth protector of claim 1 wherein the single layer is an elongated strip comprising beeswax.

9. The teeth protector of claim 1 wherein the at least one cushioning device comprises a plurality of layers having an uppermost teeth-contacting layer.

10. The teeth protector of claim 1 wherein the uppermost teeth-contacting layer comprises beeswax.

11. The teeth protector of claim 10 further comprising a pattern formed in the uppermost teeth-contacting layer.

12. An improved laryngoscope assembly for use in performing endotracheal intubation of a patient comprising:
   a. a handle;
   b. a laryngoscope blade pivotally mounted to the handle and having a front tip area, a middle portion, a back end and at least one selected surface; and
   c. a teeth protector comprising at least one cushioning device made of a deformable material such that the at least one cushioning device is capable of being deformed about the at least one selected surface of the laryngoscope blade and retains a deformed shape, the deformable material being adherent along the entire surface thereof such that the at least one cushioning device adheres to the at least one selected surface of the blade about which the cushioning device is deformed when pressed thereupon, the at least one selected surface beginning at the back end of the blade and ending at the middle portion of the blade, the deformable material further being easily removable from the at least one selected surface after use of the blade with the patient.

13. The laryngoscope assembly of claim 12 wherein the at least one cushioning device comprises beeswax.

14. The laryngoscope assembly of claim 13 further comprising a softening agent in the beeswax.

15. The laryngoscope assembly of claim 14 wherein the softening agent is a substance selected from the group consisting of vegetable oil and mineral oil.

16. The laryngoscope assembly of claim 12 wherein the teeth protector comprises a first cushioning device applied to a first selected surface, and a second cushioning device applied to a second selected surface.

17. The laryngoscope assembly of claim 16 wherein the first and second cushioning devices comprise beeswax.

18. The laryngoscope assembly of claim 12 wherein the at least one cushioning device comprises a single layer comprising beeswax.

19. The laryngoscope assembly of claim 18 further comprising a pattern formed in the single layer.

20. The laryngoscope assembly of claim 12 wherein the at least one cushioning device comprises a plurality of layers having an uppermost teeth-contacting layer.

21. The laryngoscope assembly of claim 20 wherein the uppermost teeth-contacting layer comprises beeswax.

22. The teeth protector of claim 21 further comprising a pattern formed in the uppermost teeth-contacting layer.

23. A method for protecting a patient's teeth during endotracheal intubation, comprising the steps of:
 a. providing a laryngoscope blade having a front tip area, a middle portion and a back end, and having at least one selected surface beginning at the back end of the blade and ending at the middle portion of the blade;
 b. providing at least one cushioning device made of a deformable material that is adherent along the entire surface thereof for applying to the at least one selected surface of the blade;
 c. shaping the at least one cushioning device about the at least one selected surface of the laryngoscope blade such that the device retains the shape of the at least one selected surface about which the device is formed; and
 d. applying pressure to the at least one cushioning device such that the at least one cushioning device adheres to the at least one selected surface when pressed thereupon.

24. The method of claim 23 further comprising the steps of applying multiple layers of the at least one cushioning device to the at least one selected surface of the laryngoscope blade.

25. The method of claim 23 further comprising the steps of forming a first cushioning device about a first selected surface and applying pressure to the first cushioning device to adhere the first cushioning device to the first selected surface, and forming a second cushioning device about a second selected surface and applying pressure to the second cushioning device to adhere the second cushioning device to the second selected surface.

* * * * *